(12) United States Patent
Matsushita et al.

(10) Patent No.: US 11,006,966 B2
(45) Date of Patent: May 18, 2021

(54) HEMOSTATIC DEVICE

(71) Applicant: TERUMO KABUSHIKI KAISHA, Tokyo (JP)

(72) Inventors: Shuhei Matsushita, Kanagawa (JP); Hiroshi Yagi, Aichi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 118 days.

(21) Appl. No.: 15/908,965

(22) Filed: Mar. 1, 2018

(65) Prior Publication Data
US 2018/0185032 A1    Jul. 5, 2018

Related U.S. Application Data

(63) Continuation of application No. PCT/JP2016/075910, filed on Sep. 2, 2016.

(30) Foreign Application Priority Data

Sep. 3, 2015 (JP) .............................. JP2015-174199

(51) Int. Cl.
| | | |
|---|---|---|
| *A61B 17/132* | (2006.01) | |
| *A61B 17/135* | (2006.01) | |
| *A61B 17/12* | (2006.01) | |

(52) U.S. Cl.
CPC .... *A61B 17/1325* (2013.01); *A61B 17/12009* (2013.01); *A61B 17/135* (2013.01); *A61B 17/1322* (2013.01); *A61B 2017/12004* (2013.01)

(58) Field of Classification Search
CPC ......... A61B 17/132–1355; A61B 5/022–0235; A61B 17/1322; A61B 17/1325;
(Continued)

(56) References Cited

U.S. PATENT DOCUMENTS

| 37,156 A | 12/1862 | Dunton |
|---|---|---|
| 3,905,361 A | 9/1975 | Hewson et al. |

(Continued)

FOREIGN PATENT DOCUMENTS

| CN | 1792320 A | 6/2006 |
|---|---|---|
| CN | 201029906 Y | 3/2008 |

(Continued)

OTHER PUBLICATIONS

Office Action (Examination report No. 1 for standard patent application) dated Jun. 27, 2018, by the Australian Patent Office in corresponding Australian Patent Application No. 2016317433. (5 pages).

(Continued)

*Primary Examiner* — George J Ulsh
*Assistant Examiner* — Andrew P. Restaino
(74) *Attorney, Agent, or Firm* — Buchanan Ingersoll & Rooney PC

(57) ABSTRACT

A hemostatic device includes a flexible band configured to be wrapped around a part of an arm to be subjected to hemostasis in which a radial artery and an ulnar artery are disposed, a securing portion that secures the band in a state of being wrapped around the arm, a first inflatable portion connected to the band to press a part to be subjected to hemostasis located in the radial artery by being inflated in response to injection of a fluid, a second inflatable portion disposed at a different position from the position of the first inflatable portion in the longitudinal direction of the band to press the ulnar artery by being inflated in response to injection of a fluid, and an auxiliary balloon disposed between the band and the second inflatable portion such that at least a portion overlaps the second inflatable portion and presses the second inflatable portion.

11 Claims, 7 Drawing Sheets

(58) Field of Classification Search
CPC ........ A61B 17/135; A61B 2017/12004; A61B 17/12; A61F 5/30–34
See application file for complete search history.

(56) References Cited

U.S. PATENT DOCUMENTS

| | | | |
|---|---|---|---|
| 4,469,099 | A | 9/1984 | McEwen |
| 4,920,971 | A | 5/1990 | Blessinger |
| 4,981,133 | A | 1/1991 | Rollband |
| 5,152,302 | A | 10/1992 | Fareed |
| 5,295,951 | A | 3/1994 | Fareed |
| 5,307,811 | A | 5/1994 | Sigwart et al. |
| 5,433,724 | A | 7/1995 | Kawasaki et al. |
| 5,464,420 | A | 11/1995 | Hori et al. |
| 5,496,262 | A | 3/1996 | Johnson et al. |
| 5,514,155 | A | 5/1996 | Daneshvar |
| 5,569,297 | A | 10/1996 | Makower et al. |
| 5,643,315 | A | 7/1997 | Danesshvar |
| 5,660,182 | A | 8/1997 | Kuroshaki et al. |
| 5,779,657 | A | 7/1998 | Daneshvar |
| 5,792,173 | A | 8/1998 | Breen et al. |
| 5,840,037 | A | 11/1998 | Tochikubo et al. |
| 6,007,562 | A | 12/1999 | Harren et al. |
| 6,336,901 | B1 * | 1/2002 | Itonaga ............. A61B 5/02141 600/499 |
| 6,361,496 | B1 | 3/2002 | Zikorus et al. |
| 6,527,727 | B2 | 3/2003 | Itonaga et al. |
| 6,694,821 | B2 | 2/2004 | Yamakoshi et al. |
| 6,827,727 | B2 | 12/2004 | Stalemark et al. |
| 7,498,477 | B2 | 3/2009 | Wada et al. |
| 7,927,295 | B2 | 4/2011 | Bates et al. |
| 8,034,009 | B2 | 10/2011 | Bates et al. |
| 8,481,803 | B2 | 7/2013 | Wada et al. |
| 8,481,805 | B2 | 7/2013 | Wada et al. |
| 8,524,974 | B2 | 9/2013 | Wada et al. |
| 8,759,603 | B2 | 6/2014 | Wada et al. |
| 9,895,155 | B2 | 2/2018 | Wada et al. |
| 9,936,959 | B2 | 4/2018 | Wada et al. |
| 9,949,741 | B2 | 4/2018 | Wada et al. |
| 10,219,809 | B2 | 3/2019 | Wada et al. |
| 2002/0170359 | A1 | 11/2002 | Yamakoshi et al. |
| 2003/0199922 | A1 | 10/2003 | Buckman |
| 2004/0049214 | A1 | 3/2004 | Akerfeldt |
| 2004/0098035 | A1 * | 5/2004 | Wada ................. A61B 17/1325 606/201 |
| 2004/0122469 | A1 | 6/2004 | Akerfeldt |
| 2013/0023734 | A1 | 1/2013 | Okamura |
| 2013/0245674 | A1 | 9/2013 | Wada et al. |
| 2013/0282048 | A1 | 10/2013 | Wada et al. |
| 2013/0289613 | A1 | 10/2013 | Wada et al. |
| 2013/0304111 | A1 | 11/2013 | Zhadkevich |
| 2015/0018869 | A1 * | 1/2015 | Benz ................... A61B 17/135 606/203 |
| 2015/0335334 | A1 * | 11/2015 | Pancholy ........... A61B 17/1325 606/202 |
| 2016/0213373 | A1 * | 7/2016 | Drasler .............. A61B 17/1325 |
| 2016/0338709 | A1 | 11/2016 | Wada |
| 2017/0035439 | A1 * | 2/2017 | Pancholy ........... A61B 17/1325 |
| 2018/0000491 | A1 | 1/2018 | Wada |
| 2018/0014833 | A1 | 1/2018 | Wada et al. |

FOREIGN PATENT DOCUMENTS

| | | |
|---|---|---|
| CN | 203647422 U | 6/2014 |
| EP | 0 601 756 A1 | 6/1994 |
| EP | 1 382 306 A2 | 1/2004 |
| EP | 1 671 580 A1 | 6/2006 |
| EP | 2 070 483 A2 | 6/2009 |
| EP | 2 245 998 A1 | 11/2010 |
| EP | 2 662 034 A1 | 11/2013 |
| JP | S52-107490 U | 8/1977 |
| JP | 56-33526 Y2 | 8/1981 |
| JP | 5-305093 A | 11/1993 |
| JP | 7-79983 A | 3/1995 |
| JP | 8-71077 A | 3/1996 |
| JP | 8-140990 A | 6/1996 |
| JP | 3031486 U | 9/1996 |
| JP | 10-57386 A | 3/1998 |
| JP | 2000-515773 A | 11/2000 |
| JP | 2004-154413 A | 6/2004 |
| JP | 2007-021112 A | 2/2007 |
| JP | 3136041 U | 9/2007 |
| JP | 2008-119517 A | 5/2008 |
| JP | 2014-200308 A | 10/2014 |
| JP | 2015-066028 A | 4/2015 |
| WO | WO-97/02783 A1 | 1/1997 |
| WO | WO-97/17900 A1 | 5/1997 |
| WO | WO-2012/126154 A1 | 9/2012 |

OTHER PUBLICATIONS

English translation of Written Opinion of the International Searching Authority dated Dec. 27, 2016, in corresponding International Application No. PCT/JP2016/075910 (6 pages).

The extended European Search Report dated Apr. 2, 2019, by the European Patent Office in corresponding European Patent Application No. 16842034.7-1122 (7 pages).

International Search Report (PCT/ISA/210) dated Dec. 27, 2016, by the Japanese Patent Office as the International Searching Authority for International Application No. PCT/JP2016/075910.

Written Opinion (PCT/ISA/237) dated Dec. 27, 2016, by the Japanese Patent Office as the International Searching Authority for International Application No. PCT/JP2016/075910.

Office Action (Examination report No. 2 for standard patent application) dated Feb. 26, 2019, by the Australian Patent Office in corresponding Australian Patent Application No. 2016317433. (2 pages).

U.S. Appl. No. 15/908,882, filed Mar. 1, 2018, Shuhei Matsushita et al.

Chinese Search Report dated Mar. 26, 2020, corresponding to Chinese Application 2016800511362 with English translation, 13 pages.

* cited by examiner

HEMOSTATIC DEVICE

CROSS-REFERENCES TO RELATED APPLICATIONS

This application is a continuation of International Application No. PCT/JP2016/075910 filed on Sep. 2, 2016, which claims priority to Japanese Application No. 2015-174199 filed on Sep. 3, 2015, the entire content of both of which is incorporated herein by reference.

TECHNICAL FIELD

The present invention generally relates to a hemostatic device for performing hemostasis by pressing a punctured site.

BACKGROUND ART

Recently, treatment/examination, etc. have been percutaneously performed by puncturing a blood vessel such as a radial artery, etc. of an arm, introducing an introducer sheath to a puncture site, and inserting a catheter, etc. into a lesion of the blood vessel, etc. through a lumen of the introducer sheath. When such a procedure is performed, it is necessary to perform hemostasis at the puncture site after withdrawing the introducer sheath. To perform hemostasis, there has been a known hemostatic device including a band for wrapping around the puncture site of the arm, a securing portion that secures the band in a state of being wrapping around the puncture side, and an inflatable portion that has flexibility and can press the puncture site by inflating in response to injection of a fluid. An example of such a device is disclosed in Japanese Application No. 2004-154413. This hemostatic device performs hemostasis by directly applying a pressing force acting from the inflatable portion to the puncture site.

SUMMARY OF THE INVENTION

A radial artery and an ulnar artery branch from a brachial artery near an elbow and are connected to each other in a palm. For this reason, when only the radial artery is pressed (compressed) for a long time, blood may hardly flow to the radial artery, and a blood flow rate of the ulnar artery may excessively increase. As a result, a blood flow rate of the radial artery decreases, so that the blood vessel occludes or the amount of platelets, etc. decreases, thereby requiring a long time for hemostasis at the puncture site. For this reason, for example, it is known to press the ulnar artery to reopen the occluded radial artery after performing hemostasis at the puncture site of the radial artery. An example of this is described in the following non-patent document—Ivo Bernat, M D et al., "Efficacy and Safety of Transient Ulnar Artery Compression to Recanalize Acute Radial Artery Occlusion After Transradial Catheterization", American Journal of Cardiology (U.S.), 2011, 107(11), p. 1698-1701.

In response to such a problem, for example, when an inflatable portion for pressing the ulnar artery is further provided in the above-described hemostatic device, it is considered that an excessive increase in blood flow flowing to the ulnar artery may be prevented by pressing the ulnar artery, thereby suppressing a decrease in blood flow rate of the radial artery at the time of pressing the radial artery.

However, in the hemostatic device configured as described above, the inflatable portion having flexibility that can inflate is included on the ulnar artery side, and thus there is a case in which the inflatable portion is deformed by receiving an external force, and a pressing direction of the inflatable portion is directed to an unintended direction. In such a case, the inflatable portion on the ulnar artery side may press a part other than the ulnar artery, for example, a tendon, a nerve, etc. around the ulnar artery. Further, when the hemostatic device is used for a long period of time, the inflatable portion on the ulnar artery side continues to compress the tendon, the nerve, etc., which may cause numbness or pain in a patient. For this reason, a doctor or a nurse need to perform an operation of depressurizing the inflatable portion, etc. over time to adjust a pressure on the ulnar artery by the inflatable portion.

The hemostatic device disclosed here is configured to enhance the hemostatic effect by suppressing a decrease in blood flow rate of a radial artery in an individual (patient), and reducing numbness or pain caused by pressing an ulnar artery.

A hemostatic device disclosed here includes a flexible band configured to be wrapped around an arm in which a radial artery and an ulnar artery are located, with the flexible band possessing a longitudinal extent that extends in a longitudinal direction; a securing portion that secures the flexible band on the arm while the flexible band is wrapped around the arm in a wrapped state; a first inflatable member connected to the flexible band and expandable upon being inflated in response to introducing fluid into an interior of the first inflatable member to press a part of the radial artery to be subjected to hemostasis, wherein the first inflatable member possesses oppositely facing surfaces, with the first inflatable member possessing an interior and an outwardly facing outer surface; and a second inflatable member disposed at a position spaced from the first inflatable member in a longitudinal direction of the band and expandable upon being inflated in response to introducing fluid into an interior of the second inflatable member, wherein the first inflatable member possesses oppositely facing surfaces. An auxiliary balloon is expandable upon being inflated in response to introducing fluid into an interior of the auxiliary balloon and is disposed between the flexible band and the second inflatable member at a position in which at least a portion of the auxiliary balloon overlaps the second inflatable member to press the second inflatable member when the auxiliary balloon is inflated.

According to the hemostatic device configured as described above, it is possible to enhance hemostatic effect by suppressing a decrease in blood flow rate of a radial artery using a second inflatable portion on an ulnar artery side. In addition, it is possible to adjust a direction in which the second inflatable portion presses an arm by pressing the second inflatable portion using an auxiliary balloon. In this way, it is possible to suppress pressing of a part other than the ulnar artery such as a tendon, a nerve, etc. around the ulnar artery by the second inflatable portion, and to reduce numbness or pain occurring in the arm due to pressing over a long period of time.

According to another aspect, a hemostatic device comprises: a flexible band configured to be wrapped around an individual's arm in which a radial artery and an ulnar artery are located, with the flexible band possessing a longitudinal extent that extends in a longitudinal direction, and wherein the flexible band includes two parts that engage one another when the flexible band is wrapped around the individual's arm in the wrapped state to secure the flexible band to the individual's arm; a plate connected to the flexible band and being more rigid than the flexible band, with the plate including a first portion and a second portion that are spaced apart from one another in the longitudinal direction; and a first inflatable member connected to the flexible band and possessing an interior, wherein the first portion of the plate overlies the first inflatable member so that the first inflatable member is positioned between the first portion of the plate and the individual's arm when the flexible band is wrapped around the individual's arm in the wrapped state. A first lumen communicates with the interior of the first inflatable member to introduce fluid into the interior of the first inflatable member when the flexible band is wrapped around the individual's arm in the wrapped state to expand the first inflatable member and press a part of the radial artery to be subjected to hemostasis, the first inflatable member possessing an exterior surface. A second inflatable member is connected to the flexible band and possesses an interior, with the second portion of the plate overlying the second inflatable member so that the second inflatable member is positioned between the second portion of the plate and the individual's arm when the flexible band is wrapped around the individual's arm in the wrapped state: A second lumen communicates with the interior of the second inflatable member to introduce fluid into the interior of the second inflatable member when the flexible band is wrapped around the individual's arm in the wrapped state to expand the second inflatable member and press a part of the ulnar artery. An auxiliary balloon possesses an interior and is expandable upon being inflated in response to introducing fluid into the interior of the auxiliary balloon. The auxiliary balloon is disposed between the second portion of the plate and the second inflatable member so that the auxiliary balloon presses the second inflatable member toward the ulnar artery when the auxiliary balloon is inflated.

In accordance with another aspect, a method comprises: wrapping a flexible band of a hemostatic device around at least a portion of a patient's wrist having a puncture site located in a radial artery of the patient's wrist so that the hemostatic device is in a wrapped state on the patient's wrist. The hemostatic device also comprises: a first inflatable member connected to the flexible band; a second inflatable member spaced from the first inflatable member in a longitudinal direction of the flexible band; and an auxiliary balloon between the flexible band and the second inflatable member. The wrapping of the flexible band around at least the portion of the wrist of the patient comprises wrapping the flexible band around at least the portion of the wrist of the patient so that the first inflatable member overlies the radial artery. The method additionally involves securing the hemostatic device in the wrapped state on the patient's wrist, inflating the first inflatable member to expand the first inflatable member so that the expanded first inflatable member applies a pressing force to the puncture site, wherein the inflating of the first inflatable member occurs after the securing of the hemostatic device in the wrapped state on the patient's wrist; inflating the auxiliary balloon; and inflating the second inflatable member. The inflating of the auxiliary balloon pressing the inflated second inflatable member toward the ulnar artery to prevent an excessive increase in blood flow flowing to the ulnar artery.

DETAILED DESCRIPTION

Figure 1:
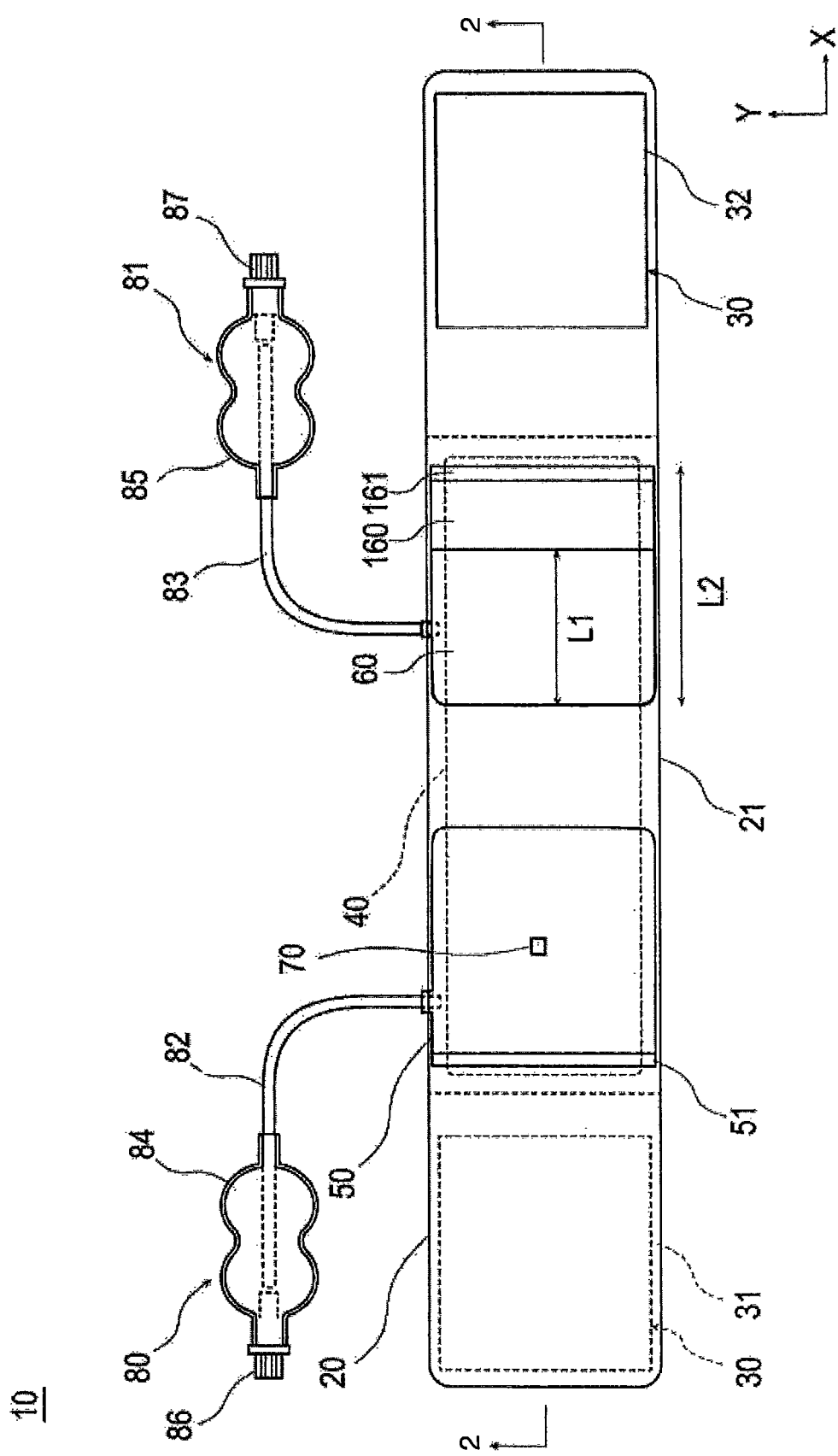
FIG. 1 is a plan view of a hemostatic device according to an embodiment viewed from an inner surface side.

Hereinafter, embodiments of the hemostatic device, representing examples of the inventive hemostatic device disclosed here, will be described with reference to the accompanying drawings. The description below does not restrict a technical scope or a meaning of terms described in claims. In addition, a ratio of dimensions in the drawings is exaggerated for convenience of description and illustration, and may be different from an actual ratio.

Figure 4:
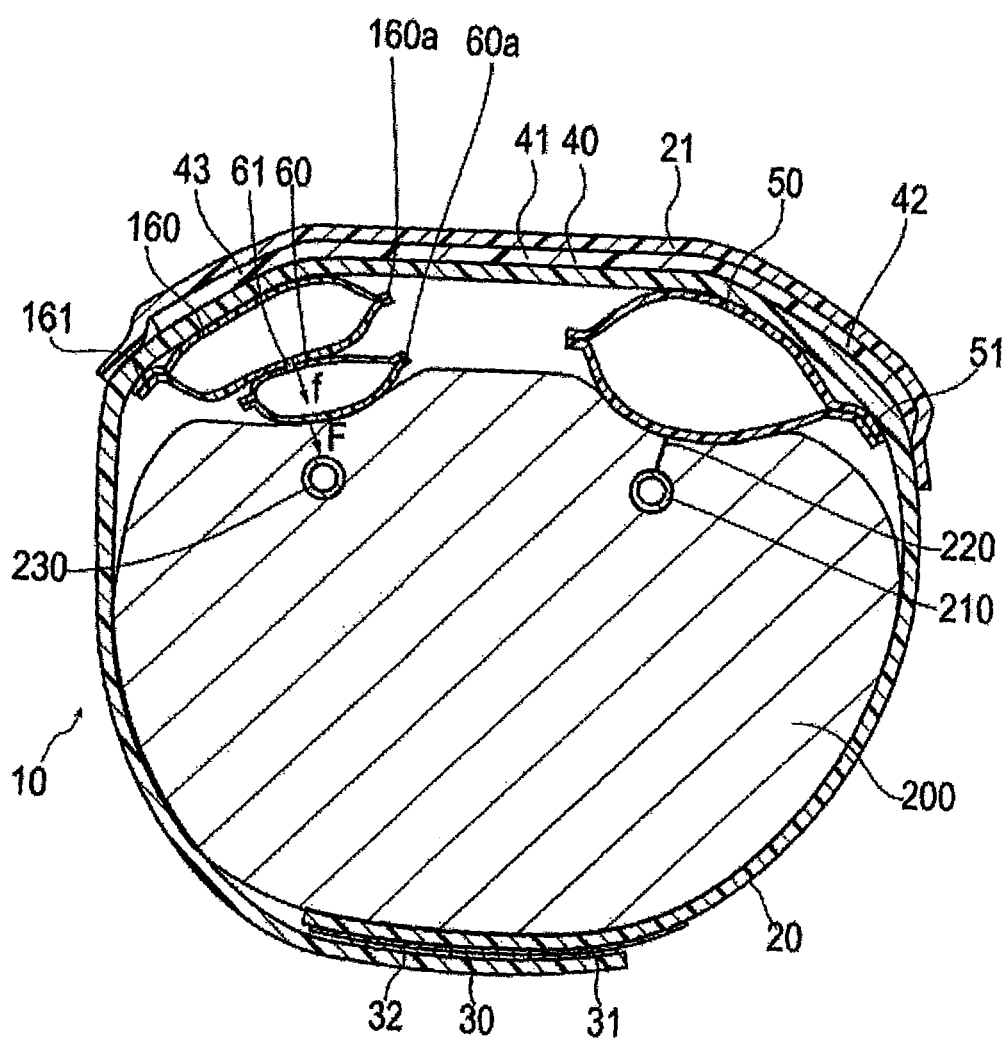
FIG. 4 is a cross-sectional view taken along the section line 4-4 of FIG. 3.

As illustrated in FIG. 4, a hemostatic device 10 according to an embodiment is used to perform hemostasis at a puncture site 220 after withdrawing an introducer sheath indwelled in the puncture site 220 (corresponding to a part to be subjected to hemostasis) formed in a radial artery 210 of a wrist 200 (corresponding to an arm) to insert a catheter, etc. performing treatment/examination, etc. into a blood vessel.

Figure 2:
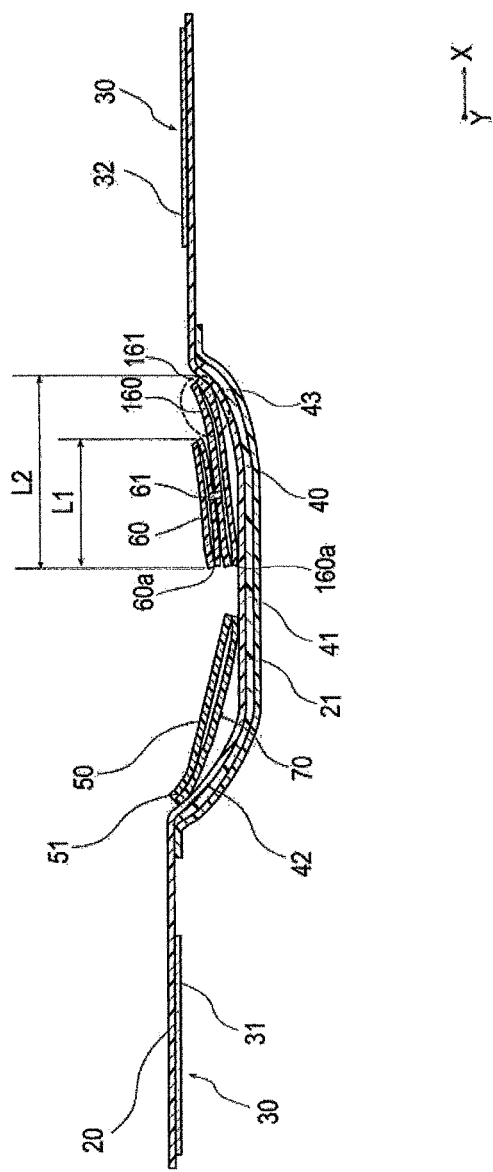
FIG. 2 is a cross-sectional view taken along the section line 2-2 of FIG. 1.

As illustrated in FIG. 1 and FIG. 2, the hemostatic device 10 may include a band 20 for wrapping around the wrist 200, a hook and loop fastener 30 (corresponding to a securing portion) for securing the band 20 while the band is in a wrapped state in which the band is wrapped around the wrist 200, a curved plate 40, a first inflatable portion or inflatable member/element 50, a second inflatable portion or inflatable member/element 60, an auxiliary balloon 160, a marker 70, a first injection portion 80, and a second injection portion 81.

In this specification, a side (mounting surface side) of the band 20 facing a body surface of the wrist 200 is referred to as an "inner surface side", and an opposite side of the band 20 is referred to as an "outer surface side" when the band 20 is wrapped around the wrist 200.

In addition, in the drawings, a longitudinal direction of the band 20 is indicated as an arrow X, and a direction orthogonal to the longitudinal direction of the band 20 is indicated as an arrow Y.

The band 20 may be a flexible band-shaped member possessing a longitudinal extent that extends in the longitudinal direction. As illustrated in FIG. 4, the band 20 may be wrapped around an outer periphery of the wrist 200 substantially once. As illustrated in FIG. 2, a curved plate holding portion 21 that holds the curved plate 40 is formed at a central portion of the band 20 (central portion in the longitudinal direction X of the band 20). The curved plate holding portion 21 may be doubled by separate band-shaped members joined to an outer surface side (or inner surface side) using a method such as fusing (heat-fusing, high-frequency fusing, ultrasonic fusing, etc.), adhesion (adhesion by an adhesive or a solvent), etc. and holds the curved plate 40 positioned in a gap between the two separate band-shaped members.

Figure 3:
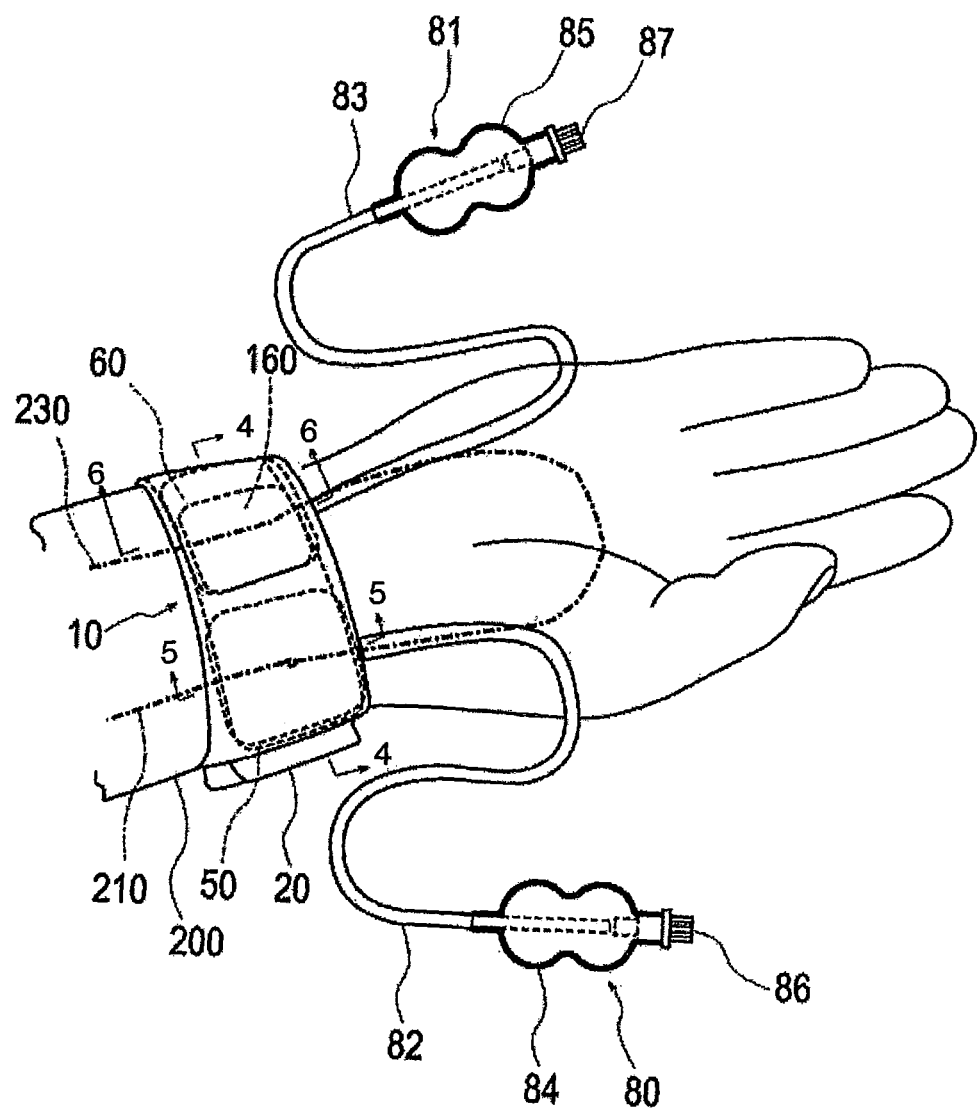
FIG. 3 is a perspective view illustrating a state of mounting the hemostatic device according to the embodiment.

A male side (or a female side) 31 of the hook and loop fastener 30 generally referred to as Magic Tape (registered trademark), etc. may be disposed on the outer surface side of the band 20 near a left end of FIG. 1, and a female side (or a male side) 32 of the hook and loop fastener 30 is disposed on the inner surface side of the band 20 near a right end of FIG. 1. As illustrated in FIG. 3 and FIG. 4, the band 20 is wrapped around the wrist 200, and the male side 31 and the female side 32 are joined together, thereby mounting the band 20 on the wrist 200. The means for securing the band 20 to the wrist 200 in a wrapped state is not limited to the hook and loop fastener 30. For example, the means for securing may correspond to a snap, a button, a clip, or a frame member passing an end portion of the band 20.

A constituent material forming the band 20 is not particularly limited as long as the material has flexibility, and examples of the material for forming the band 20 include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

The band 20 is preferably substantially transparent. However, the band 20 may not be transparent, and may be translucent or colored transparent. In this way, the puncture site 220 may be visually recognized from the outer surface side, and the marker 70 described below may be relatively easily positioned in the puncture site 220.

As illustrated in FIG. 2, the plate 40 may be a curved plate 40 held in the band 20 by being inserted into or positioned in the doubly formed curved plate holding portion 21 of the band 20. The plate 40 in the illustrated example includes an inner surface on the side of the inflatable members 50, 60, and the plate 40 is curved so that portions of the inner surface of the plate are curved. The curved plate 40 may be made of a material more rigid than the material of the band 20 (the plate 40 is more rigid than the flexible band 20) and may maintain a substantially constant shape.

The curved plate 40 has a shape elongated in the longitudinal direction (a direction of an arrow X) of the band 20. A central portion 41 of the curved plate 40 in the longitudinal direction may have a flat plate shape almost without being curved, and a first curved portion 42 (left side of FIG. 2) and a second curved portion 43 (right side of FIG. 2) curved toward an inner peripheral side and along the longitudinal direction of the band 20 (a circumferential direction of the wrist 200) are formed at both sides of the central portion 41, respectively. FIGS. 2 and 4 show that the first curved portion 42 possesses a radius of curvature smaller than the inner surface of central portion 41. Additionally, FIGS. 2 and 4 show that the first curved portion 42 possesses a curvature (curvature is a reciprocal of a radius of curvature) greater than the curvature of the inner surface of central portion 41. FIGS. 2 and 4 also illustrate that the second curved portion 43 possesses a radius of curvature smaller than the inner surface of central portion 41, and that the second curved portion 43 possesses a curvature greater than the curvature of the inner surface of the central portion 41.

A constituent material forming the curved plate 40 is not particularly limited as long as the puncture site 220 can be visually recognized. Examples of the material include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

Similar to the band 20, the curved plate 40 is preferably substantially transparent. However, the curved plate 40 may not be transparent, and may be translucent or colored transparent. In this way, the puncture site 220 may be reliably visually recognized from the outer surface side, and the marker 70 described below may be relatively easily positioned in the puncture site 220. The curved plate 40 may not have a non-curved part such as the central portion 41, that is, may be curved over an entire length of the plate 40.

The first inflatable portion 50 and the auxiliary balloon 160 connected to the second inflatable portion 60, are connected to the band 20. The first inflatable portion 50, the second inflatable portion 60, and the auxiliary balloon 160 inflate by being injected with a fluid (gas such as air or liquid). The first inflatable portion 50 presses the puncture site 220 located in the radial artery 210 of the wrist 200. The second inflatable portion 60 presses an ulnar artery 230 by pressing the body surface of the wrist 200.

As illustrated in FIG. 2, the first inflatable portion 50 is located to overlap the vicinity of a part between the first curved portion 42 on a left end side of FIG. 2 and the central portion 41 of the curved plate 40.

A constituent material from which the first inflatable portion 50 is fabricated is not particularly limited as long as the material has flexibility. For example, it is possible to use the same material as the constituent material of the band 20 mentioned above.

Similar to the band 20 and the curved plate 40, the first inflatable portion 50 is preferably substantially transparent. In this way, the puncture site 220 may be visually recognized from the outer surface side, and the marker 70 described below may be rather easily positioned in the puncture site 220.

For example, as illustrated in FIG. 2, the first inflatable portion 50 may be formed in a shape of a bag obtained by overlapping two sheet materials made of the above-described materials and joining edge portions using a method such as fusing, adhesion, etc. As illustrated in FIG. 1, an external shape of the first inflatable portion 50 is a rectangle in a state of not being inflated.

As illustrated in FIG. 2, the first inflatable portion 50 may be connected to the band 20 through a first holding portion 51 having flexibility. The first holding portion 51 is preferably provided on the first curved portion 42 side of the curved plate 40. In addition, the first holding portion 51 is preferably made of the same material as that of the first inflatable portion 50. In this way, joining the first holding portion 51 of the first inflatable portion 50 to the band 20 by fusing may be relatively easily performed, and manufacture may be rather easily accomplished.

As illustrated in FIG. 2, the second inflatable portion 60 is disposed at a different position from that of the first inflatable portion 50 in the longitudinal direction of the band 20 to overlap the vicinity of a part between the second curved portion 43 and the central portion 41.

Similar to the first inflatable portion 50, a constituent material forming the second inflatable portion 60 preferably corresponds to a material having flexibility. For example, it is possible to use the same material as the constituent material forming the band 20 mentioned above. Similar to the band 20 and the curved plate 40, and the first inflatable portion 50, the second inflatable portion 60, is preferably substantially transparent.

Similar to the first inflatable portion 50, a structure of the second inflatable portion 60 may be formed in a shape of a bag obtained by overlapping two sheet materials made of the above-described materials and joining edge portions using a method such as fusing, adhesion, etc. As illustrated in FIG. 1, an external shape of the second inflatable portion 60 is a rectangle in a state of not being inflated.

As illustrated in FIG. 2, the auxiliary balloon 160 may be disposed between the band 20 and the second inflatable portion 60 such that at least a portion of the auxiliary balloon 160 overlaps the second inflatable portion 60. The auxiliary balloon 160 is interposed between a surface of the wrist 200 and the curved plate 40 at the time of wrapping the hemostatic device 10 around the wrist 200, and thus is inflated by a pressure of a fluid (gas such as air or liquid) filled in the auxiliary balloon 160 to press the second inflatable portion 60. The auxiliary balloon 160 and the second inflatable portion 60 may be joined together by a method such as fusing, adhesion, etc. A communication path 61 that allows communication between an inside of the auxiliary balloon 160 and an inside of the second inflatable portion 60 is provided. When the fluid is supplied to the auxiliary balloon 160, the fluid injected into the auxiliary balloon 160 through the communication path 61 is injected into the second inflatable portion 60.

As illustrated in FIG. 1 and FIG. 2, a length L2 of the auxiliary balloon 160 along the longitudinal direction of the band 20 may be longer than a length L1 of the second inflatable portion 60 along the longitudinal direction of the band 20. Further, in a state before inflation of the second inflatable portion 60 and the auxiliary balloon 160, an end portion 160a of the auxiliary balloon 160 on the first inflatable portion 50 side (left side of FIG. 2) may be disposed to overlap with an end portion 60a of the second inflatable portion 60 on the first inflatable portion 50 side (left side of FIG. 2). In this way, a part of the auxiliary balloon 160 on the opposite side from the first inflatable portion 50 (right side of FIG. 2) corresponds to a part not overlapping with the second inflatable portion 60 (a part surrounded by a dotted line in FIG. 2). In other words, one end portion of the auxiliary balloon 160 extends beyond the second inflatable portion 60. The non-overlapping part does not receive a repulsive force by the second inflatable portion 60 when the second inflatable portion 60 inflates, and thus is likely to be inflated and deformed when compared to a part overlapping with the second inflatable portion 60. For this reason, as illustrated in FIG. 4, at the time of inflation, the second inflatable portion 60 is pressed from the outer surface side to the first inflatable portion 50 side (right side in FIG. 4). That is, the auxiliary balloon 160 inflates to press the second inflatable portion 60 in a direction substantially toward the ulnar artery 230 as indicated by an arrow fin FIG. 4. By receiving a pressing force from the auxiliary balloon 160, the second inflatable portion 60 may be pressed in an inclined (oblique) direction indicated by an arrow F of FIG. 4 rather than a vertical direction from a top to a bottom (a direction perpendicular to the surface of the wrist 200).

As illustrated in FIG. 2, similar to the first inflatable portion 50, the auxiliary balloon 160 may be connected to the band 20 through the second holding portion 161 having flexibility. The second holding portion 161 is preferably provided on the second curved portion 43 side of the curved plate 40. In addition, the second holding portion 161 is preferably made of the same material as that of the auxiliary balloon 160. In this way, joining the second holding portion 161 to the band 20 by fusing may be rather easily performed, and manufacture may be easily performed.

Similar to the second inflatable portion 60, a constituent material forming the auxiliary balloon 160 preferably corresponds to a flexible material. For example, it is possible to use the same material as the constituent material of the second inflatable portion 60 mentioned above. Joining to the second inflatable portion 60 by fusing may be easily performed using the same material as that of the second inflatable portion 60. Similar to the band 20, the curved plate 40, the first inflatable portion 50, and the second inflatable portion 60, it is preferable that the auxiliary balloon 160 is substantially transparent.

As illustrated in FIG. 2, the marker 70 may be provided on the outer surface side of the first inflatable portion 50, that is, on a surface of the first inflatable portion 50 not facing the body surface of the wrist 200. When such a marker 70 is provided in the first inflatable portion 50, the first inflatable portion 50 may be relatively easily positioned with respect to the puncture site 220, and thus a position shift of the first inflatable portion 50 is suppressed.

A shape of the marker 70 is not particularly limited. Examples of the shape include a circle, a triangle, a rectangle, etc. In the present embodiment, the shape corresponds to the rectangle.

A size of the marker 70 is not particularly limited. However, considering an example in which the shape of the marker 70 is rectangular, a length of a side of the rectangular marker 70 is preferably in a range of 1 to 4 mm. When the length of the side is 5 mm or more, the size of the marker 70 becomes larger when compared to a size of the puncture site 220, and thus it may be difficult to position a central portion 52 of the first inflatable portion 50 in the puncture site 220.

A material of the marker 70 is not particularly limited. Examples of such material include an oily coloring agent such as ink, a resin kneaded with a pigment, etc.

A color of the marker 70 is not particularly limited so long as the color allows the first inflatable portion 50 to be positioned in the puncture site 220. However, a green-based color is preferable. When the green-based color is adopted, it is relatively easy to visually recognize the marker 70 on blood or skin, and thus the first inflatable portion 50 is more easily positioned in the puncture site 220.

In addition, the marker 70 is preferably translucent or colored transparent. In this way, the puncture site 220 may be visually recognized from an outer surface side of the marker 70.

The manner in which the marker 70 is provided at the first inflatable portion 50 is not particularly limited. Examples include printing the marker 70 on the first inflatable portion 50, fusing the marker 70 to the first inflatable portion 50, applying an adhesive to one surface of the marker 70 to paste the marker 70 to the first inflatable portion 50, etc.

The marker 70 may be provided on the inner surface side of the first inflatable portion 50. In this instance, the marker 70 is preferably provided on an inner surface, etc. in the first inflatable portion 50 so as not to directly come into contact with the puncture site 220.

The first injection portion 80 and the second injection portion 81 are parts for injecting a fluid into the first inflatable portion 50 and the second inflatable portion 60, respectively, and are connected to the first inflatable portion 50 and the second inflatable portion 60, respectively, as illustrated in FIG. 1.

The first injection portion 80 includes a flexible first tube 82 having a proximal portion connected to the first inflatable portion 50 and a lumen communicating with an inside of the first inflatable portion 50, a first bag body 84 disposed at a distal portion of the first tube 82 to communicate with the lumen of the first tube 82, and a tube-shaped first connector 86 connected to the first bag body 84. A check valve (not illustrated) is incorporated in the first connector 86.

Similar, the second injection portion 81 includes a flexible second tube 83 having a proximal portion connected to the auxiliary balloon 160 and a lumen communicating with an inside of the second inflatable portion 60, a second bag body 85 disposed at a distal portion of the second tube 83 to communicate with the lumen of the second tube 83, and a tube-shaped second connector 87 connected to the second bag body 85. A check valve (not illustrated) is incorporated in the second connector 87.

At the time of inflating (expanding) the first inflatable portion 50, a tip of a syringe (not illustrated) is inserted into the first connector 86 to open the check valve, and a plunger of this syringe is pushed to inject a fluid in the syringe into the first inflatable portion 50 through the first injection portion 80. When the first inflatable portion 50 expands, the first bag body 84 communicating with the first inflatable portion 50 through the first tube 82 also expands, and it is possible to visually confirm that the first inflatable portion 50 can be pressed without leakage of the fluid. When the tip of the syringe is withdrawn from the first connector 86 after the fluid is injected into the first inflatable portion 50, the check valve incorporated in the first connector 86 is closed to prevent leakage of the fluid, and an expanded state of the first inflatable portion 50 is maintained.

Figure 5:
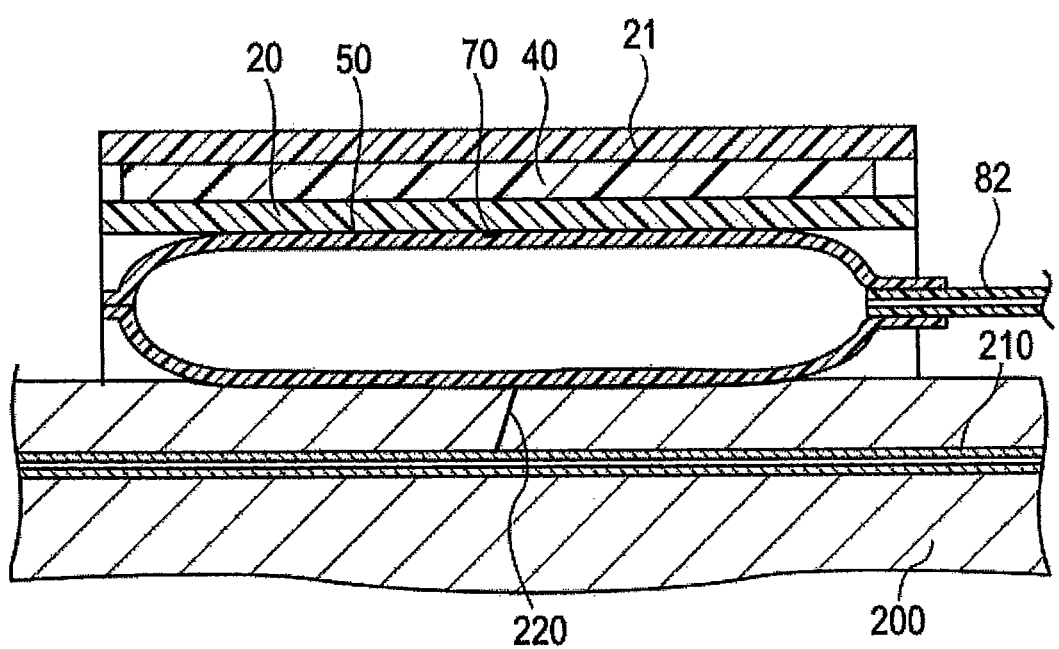
FIG. 5 is a cross-sectional view taken along the section line 5-5 of FIG. 3.
Figure 6:
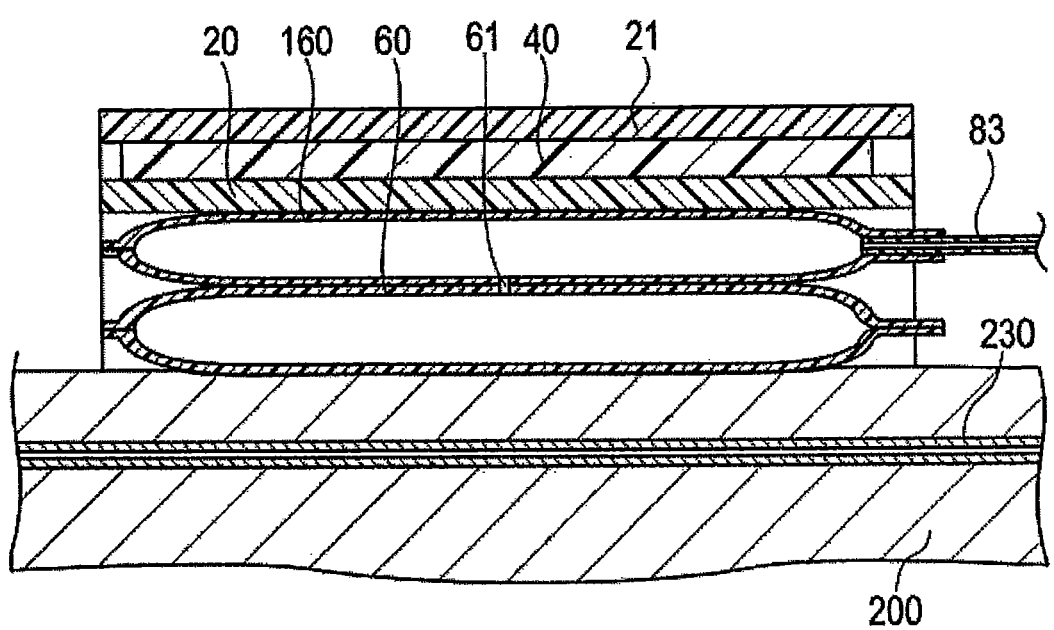
FIG. 6 is a cross-sectional view taken along the section line 6-6 of FIG. 3.

When the same operation is performed with respect to the second injection portion 81 connected to the second inflatable portion 60 and the auxiliary balloon 160, an expanded state of the second inflatable portion 60 and the auxiliary balloon 160 is maintained. In this way, as illustrated in FIG. 4 to FIG. 6, the first inflatable portion 50, the second inflatable portion 60, and the auxiliary balloon 160 inflate. The second tube 83 is preferably disposed on the same side as a side where the first tube 82 is disposed with respect to the band 20. In this way, it is possible to inject a fluid into the first tube 82 and the second tube 83 from the same side. For this reason, when the same syringe is used for the first tube 82 and the second tube 83, it is possible to relatively easily perform an operation of inserting and withdrawing the syringe.

Next, a description will be given of a manner or method of using the hemostatic device 10 according to the present embodiment representing an example of an operation method that can be employed.

Before the hemostatic device 10 is mounted on the wrist 200, the first inflatable portion 50, the second inflatable portion 60, and the auxiliary balloon 160 are in a state of not being inflated. When the wrist 200 is punctured, the puncture site 220 with respect to the radial artery 210 is normally biased to a thumb side of the right hand wrist 200. Normally, the introducer sheath is indwelled in the puncture site 220. The band 20 is wrapped around the wrist 200 in which the introducer sheath is indwelled, the first inflatable portion 50 and the band 20 are positioned such that the marker 70 provided in the first inflatable portion 50 overlaps the puncture site 220, and the male side 31 and the female side 32 of the hook and loop fastener 30 are brought into contact with each other and joined to each other, thereby mounting the band 20 on the wrist 200 so that the hemostatic device is secured on the patient's wrist.

The hemostatic device 10 is mounted on the wrist 200 such that the first injection portion 80 and the second injection portion 81 face a downstream side of a blood flow of the radial artery 210. In this way, the first injection portion 80 and the second injection portion 81 may be operated without interfering with manipulation on the upstream side of the wrist or a device (for example, a sphygmomanometer, etc.) located on the upstream side. In addition, when the hemostatic device 10 is mounted on the right hand wrist 200 such that the first injection portion 80 and the second injection portion 81 face the downstream side, the first inflatable portion 50 is located on the radial artery 210 biased to the thumb side of the wrist 200, and the second inflatable portion 60 is located around the ulnar artery 230. In the case of the artery, the upstream side of the blood vessel refers to a direction of the blood vessel approaching the heart. In addition, the downstream side of the blood vessel refers to a direction of the blood vessel away from the heart.

After the hemostatic device 10 is mounted on the wrist 200, the syringe (not illustrated) is connected to the first connector 86 of the first injection portion 80, the fluid is injected into the first inflatable portion 50 as described above, and the first inflatable portion 50 is inflated to press the puncture site 220 as illustrated in FIG. 4 and FIG. 5. A degree of inflation of the first inflatable portion 50, that is, a pressing force applied to the puncture site 220 located in the radial artery 210 may be rather easily adjusted depending on the case according to an injection amount of the fluid at this time.

After the first inflatable portion 50 is inflated, the syringe is detached from the first connector 86. Then, the introducer sheath is withdrawn from the puncture site 220. In this way, the first inflatable portion 50 maintains an inflated state, and a state of pressing the puncture site 220 is maintained.

Subsequently, when the syringe is connected to the second connector 87 of the second injection portion 81, and the fluid is injected into the auxiliary balloon 160 as described above, the auxiliary balloon 160 and the second inflatable portion 60 inflate. Note that the second inflatable portion inflates when a fluid, which is injected into the auxiliary balloon 160 through the communication path 61, is injected. Here, a pressing force of the second inflatable portion 60 to the ulnar artery 230 may be rather easily adjusted by the amount of the fluid injected into the auxiliary balloon 160 and the second inflatable portion 60.

When the first inflatable portion 50, the second inflatable portion 60, and the auxiliary balloon 160 are inflated, the curved plate 40 is separated from the body surface of the wrist 200 and hardly comes into contact with the wrist 200. In addition, when the first inflatable portion 50, the second inflatable portion 60, and the auxiliary balloon 160 are inflated after the hemostatic device 10 is mounted, inflation of the first inflatable portion 50, the second inflatable portion 60, and the auxiliary balloon 160 in a direction away from the body surface of the wrist 200 is suppressed by the curved plate 40, and a pressing force of the first inflatable portion 50 and the second inflatable portion 60 is concentrated on the wrist 200 side. For this reason, a pressing force from the first inflatable portion 50 intensively acts on the vicinity of the puncture site 220, and thus the hemostatic effect may be improved.

In addition, when the first inflatable portion 50 presses the radial artery 210, the ulnar artery 230 may be pressed, thereby preventing an excessive increase in the blood flow flowing to the ulnar artery 230, and suppressing a decrease in the blood flow rate of the radial artery 210. In this way, occlusion of the blood vessel may be prevented, and a decrease in the amount of the platelets, etc. may be suppressed, thereby performing hemostasis at the puncture site 220 in a relatively short time.

When hemostasis is completed, the pressing force of the first inflatable portion 50 to the puncture site 220 is further reduced and the hemostatic device 10 is removed.

When hemostasis in the puncture site 220 is completed and the hemostatic device 10 is removed, the first inflatable portion 50 is contracted, and then the male side 31 and the female side 32 of the hook and loop fastener 30 are peeled off to remove the hemostatic device 10 from the wrist 200. The first inflatable portion 50 may not be contracted (deflated) when the hemostatic device 10 is removed.

As described above, the hemostatic device 10 according to the present embodiment includes the flexible band 20 that can be wrapped around the wrist 200 in which the radial artery 210 and the ulnar artery 230 run, the hook and loop fastener 30 that secures the band 20 in a state of being wrapped around the wrist 200, the first inflatable portion 50 connected to the band 20 and allowed to press a part to be subjected to hemostasis located in the radial artery 210 by being inflated in response to injection of the fluid, the second inflatable portion 60 disposed at a different position from that of the first inflatable portion 50 in the longitudinal direction of the band 20 and allowed to press the ulnar artery 230 by being inflated in response to injection of the fluid, and the auxiliary balloon 160 disposed between the band 20 and the second inflatable portion 60 such that at least a portion overlaps with the second inflatable portion 60 and allowed to press the second inflatable portion 60.

According to the hemostatic device 10 configured as described above, it is possible to enhance the hemostatic effect by suppressing a decrease in the blood flow rate of the radial artery 210 using the second inflatable portion 60 on the ulnar artery 230 side. In addition, it is possible to adjust a direction in which the second inflatable portion 60 presses the wrist 200 by pressing the second inflatable portion 60 using the auxiliary balloon 160. In this way, it is possible to restrict pressing a part other than the ulnar artery 230 such as a tendon, a nerve, etc. around the ulnar artery 230 by the second inflatable portion 60, and to reduce numbness or pain occurring on the wrist 200 due to pressing over a long period of time.

In addition, the length L2 of the auxiliary balloon 160 along the longitudinal direction of the band 20 is longer than the length L1 of the second inflatable portion 60 along the longitudinal direction of the band 20. In this way, the auxiliary balloon 160 disposed on the outer surface side may apply a pressing force across the whole outer surface of the second inflatable portion 60 along the longitudinal direction of the band 20. Therefore, when the second inflatable portion 60 and the auxiliary balloon 160 are inflated, the second inflatable portion 60 may be held on the inner surface side of the auxiliary balloon 160, and the second inflatable portion 60 may be inhibited from moving in an unintended direction.

In addition, in a state before inflation of the second inflatable portion 60 and the auxiliary balloon 160, the end portion 160a of the auxiliary balloon 160 on the first inflatable portion 50 side may overlap the end portion 60a of the second inflatable portion 60 on the first inflatable portion 50 side. In this way, a pressing direction of the second inflatable portion 60 may be inclined and adjusted by the auxiliary balloon 160 so as to be directed toward the ulnar artery 230 side.

In addition, the inside of the second inflatable portion 60 communicates with the inside of the auxiliary balloon 160, and the second injection portion 81 that injects a fluid is connected to the auxiliary balloon 160. Since the second inflatable portion 60 and the auxiliary balloon 160 can be inflated by a single operation, the operation is facilitated.

(Modification)

Figure 7:
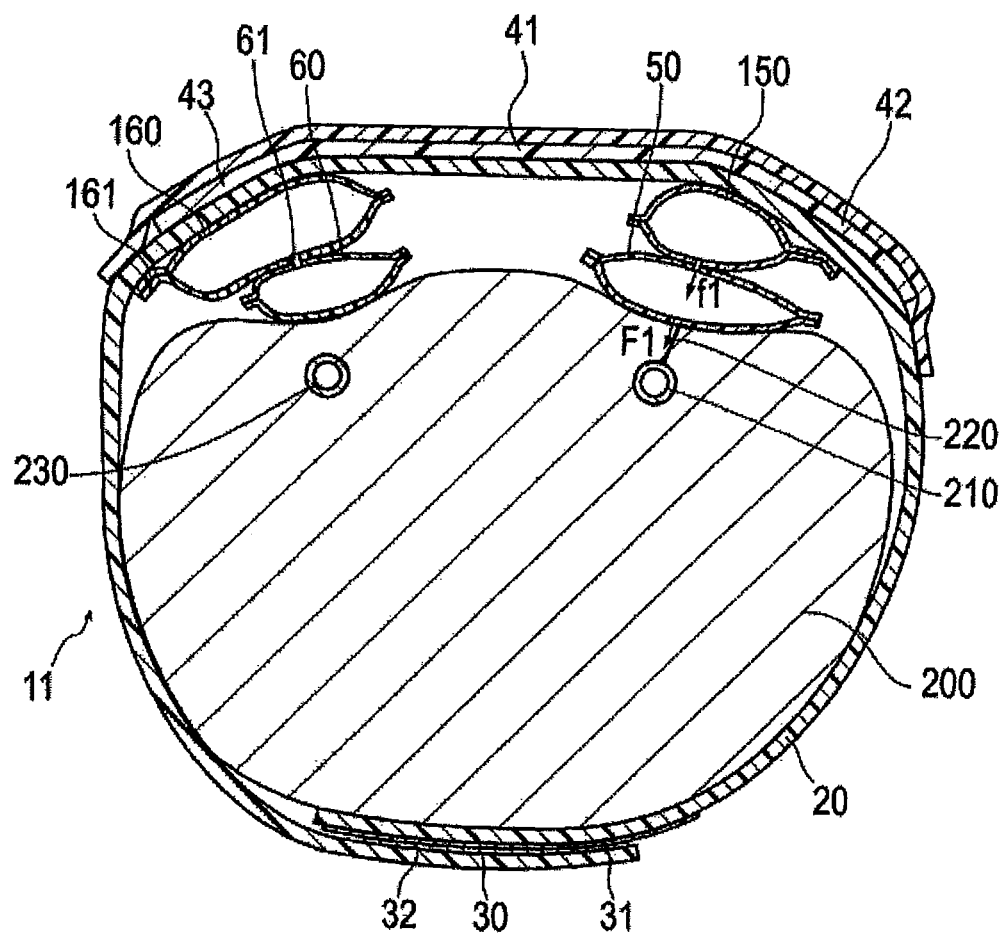
FIG. 7 is a cross-sectional view corresponding to FIG. 4, as a drawing illustrating a state of mounting a hemostatic device according to a modification of the embodiment.

A hemostatic device 11 according to a modification further includes an auxiliary compressing portion 150 between the first inflatable portion 50 and the band 20. That is, the embodiment described above and shown in FIGS. 1-6 include a single inflatable portion or member 50 on one side of the center portion of the plate, whereas in the modification, two inflatable portions or members are provided on the one side of the center portion of the plate. The other aspects of the hemostatic device are substantially the same as that of the above-described embodiment. In the description below, features that are the same or similar to those described above are identified by the same reference numerals and a detailed description of such features is not repeated As illustrated in FIG. 7, the auxiliary compressing portion 150 overlaps the first inflatable portion 50 and is positioned between the first inflatable portion 50 and the band 20. The auxiliary compressing portion 150 may be made of a flexible material, and presses the first inflatable portion 50 by being inflated in response to injection of a fluid. The auxiliary compressing portion 150 functions as a pressing member that presses the first inflatable portion 50. The auxiliary compressing portion 150 may communicate with the first inflatable portion 50 and inflates when the first inflatable portion 50 is inflated by being injected with a fluid.

The auxiliary compressing portion 150 may be interposed between the surface of the wrist 200 and the curved plate 40 when the hemostatic device 11 is mounted on the wrist 200, and thus inflates by a pressure of a fluid filled or introduced into the interior of the auxiliary compressing portion 150 to press the first inflatable portion 50 substantially in a direction toward the puncture site 220 (a direction of an arrow f1) as illustrated in FIG. 7. By receiving such a pressing force from the auxiliary compressing portion 150, the first inflatable portion 50 may be pressed in an inclined or oblique direction indicated by an arrow F1 of FIG. 7 rather than a vertical direction from a top to a bottom (a direction perpendicular to the surface of the wrist 200). In this way, more excellent hemostatic effect may be obtained when compared to a case in which the puncture site 220 is pressed in the vertical direction from the top to the bottom.

The auxiliary compressing portion 150 is not limited to the above configuration, and may correspond to, for example, a member made of a sponge-like substance, an elastic material, an aggregate of fibers such as cotton, a combination thereof, etc.

As described above, the hemostatic device 11 according to the modification further includes the auxiliary compressing portion 150, so that a pressing direction of the first inflatable portion 50 against the wrist 200 may be relatively easily adjusted, thereby improving operability and further improving the hemostatic effect.

Even though the hemostatic device disclosed here has been described by way of example through the embodiment and the modification, the invention is not limited only to each configuration described above, and may be appropriately modified based on description in claims.

For example, each portion included in the hemostatic device may be replaced with a portion having an arbitrary configuration capable of exerting the same function. In addition, an arbitrary component may be added.

In addition, the invention is not limited to the hemostatic device used by being mounted on the wrist, and is applicable to a hemostatic device used by being mounted on any part of the arm in which the radial artery and the ulnar artery run.

In addition, even though the length of the auxiliary balloon along the longitudinal direction of the band may be longer than the length of the second inflatable portion along the longitudinal direction of the band as described above, the invention is not limited thereto, and the length of the auxiliary balloon may be less than or equal to the length of the second inflatable portion.

In addition, in the state before inflation of the second inflatable portion and the auxiliary balloon, the end portion of the auxiliary balloon on the first inflatable portion side is disposed to overlap the end portion of the second inflatable portion on the first inflatable portion side. However, arrangement of the auxiliary balloon is not limited thereto, and the auxiliary balloon may be disposed such that at least a portion overlaps the second inflatable portion. For example, the end portion of the auxiliary balloon on the opposite side from the side where the first inflatable portion is disposed may overlap the end portion of the second inflatable portion on the opposite side from the side where the first inflatable portion is disposed.

In addition, a description has been given of a configuration including one auxiliary balloon. However, it is possible to adopt a configuration including two or more auxiliary balloons. In this case, referring to lengths of the auxiliary balloons in the longitudinal direction of the band, it is preferable that a length of an auxiliary balloon disposed on the outer surface side is longer than a length of an auxiliary balloon disposed on the inner surface side.

In addition, the second injection portion is connected to the auxiliary balloon. However, the invention is not limited thereto, and the second injection portion may be connected to the second inflatable portion.

In addition, the external shapes of the first inflatable portion and the second inflatable portion are not limited to the rectangular shape in the state of not being inflated. For example, it is possible to configure the first inflatable portion and the second inflatable portion as a circle, an ellipse, or a polygon such as a pentagon.

In addition, the marker may not be provided at the first inflatable portion, and may be provided in the band, the curved plate, or the auxiliary compressing portion. In addition, the marker is more preferably provided to overlap the central portion of the first inflatable portion.

The detailed description above describes embodiments of a hemostatic device representing examples of the inventive hemostatic device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
a flexible band configured to be wrapped around an individual's arm in which a radial artery and an ulnar artery are located, the flexible band possessing a longitudinal extent that extends in a longitudinal direction;
the flexible band including two parts that engage one another when the flexible band is wrapped around the individual's arm in a wrapped state to secure the flexible band to the individual's arm;
a plate connected to the flexible band, the plate being more rigid than the flexible band, the plate including a first portion and a second portion that are spaced apart from one another in the longitudinal direction;
a first inflatable member connected to the flexible band and possessing an interior, the first portion of the plate overlying the first inflatable member so that the first inflatable member is positioned between the first portion of the plate and the individual's arm when the flexible band is wrapped around the individual's arm in the wrapped state;
a first lumen in communication with the interior of the first inflatable member to introduce fluid into the interior of the first inflatable member when the flexible band is wrapped around the individual's arm in the wrapped state to expand the first inflatable member and press a part of the radial artery to be subjected to hemostasis, the first inflatable member possessing an exterior surface;
a second inflatable member connected to the flexible band and possessing an interior, the second portion of the plate overlying the second inflatable member so that the second inflatable member is positioned between the second portion of the plate and the individual's arm when the flexible band is wrapped around the individual's arm in the wrapped state;
a second lumen in communication with the interior of the second inflatable member to introduce fluid into the interior of the second inflatable member when the flexible band is wrapped around the individual's arm in the wrapped state to expand the second inflatable member and press a part of the ulnar artery; and
an auxiliary balloon possessing an interior and expandable upon being inflated in response to introducing fluid into the interior of the auxiliary balloon, the auxiliary balloon being disposed between the second portion of the plate and the second inflatable member so that the auxiliary balloon directly presses the second inflatable member toward the ulnar artery when the auxiliary balloon is inflated,
wherein the second inflatable member possesses a length in the longitudinal direction of the flexible band and the auxiliary balloon possesses a length in the longitudinal direction of the flexible band, the length of the auxiliary balloon being greater than the length of the second inflatable member, and
wherein the second inflatable member includes two ends, one of the ends being located closer to the first inflatable member in the longitudinal direction of the flexible band than the other end, the auxiliary balloon including opposite end portions, one of the end portions of the auxiliary balloon being located closer to the first inflatable member in the longitudinal direction of the flexible band than the other end portion of the auxiliary balloon, the one end portion of the auxiliary balloon being located at the one end of the second inflatable member in a direction orthogonal to the longitudinal direction of the flexible band before inflation of the second inflatable member and the auxiliary balloon.

2. The hemostatic device according to claim 1, further comprising a communication path communicating the interior of the auxiliary balloon with the interior of the second inflatable member.

3. The hemostatic device according to claim 1, wherein the plate possesses an inner surface, the inner surface being curved at the first and second portions of the inner plate.

4. The hemostatic device according to claim 1, wherein the first inflatable member is connected to the flexible band by virtue of one end portion of the first inflatable member being fixed to the flexible band, and the second inflatable member is connected to the flexible band by virtue of one end portion of the second inflatable member being fixed to the flexible band.

5. The hemostatic device according to claim 1, further comprising an auxiliary compressing member expandable upon being inflated in response to introducing fluid into an interior of the auxiliary compressing member and disposed between the flexible band and the first inflatable member at a position in which at least a part of the auxiliary compressing member overlaps the first inflatable member to press the first inflatable member when the auxiliary compressing member is inflated.

6. A hemostatic device comprising:
a flexible band configured to be wrapped around an arm in which a radial artery and an ulnar artery are located, the flexible band possessing a longitudinal extent that extends in a longitudinal direction;
a securing portion that secures the flexible band on the arm while the flexible band is wrapped around the arm in a wrapped state;
a first inflatable member connected to the flexible band and expandable upon being inflated in response to introducing fluid into an interior of the first inflatable member to press a part of the radial artery to be subjected to hemostasis, the first inflatable member possessing oppositely facing surfaces;
a second inflatable member disposed at a position spaced from the first inflatable member in the longitudinal direction of the flexible band and expandable upon being inflated in response to introducing fluid into an interior of the second inflatable member, the second inflatable member possessing oppositely facing surfaces; and
an auxiliary balloon expandable upon being inflated in response to introducing fluid into an interior of the auxiliary balloon and disposed between the flexible band and the second inflatable member at a position in which at least a portion of the auxiliary balloon overlaps the second inflatable member to directly press the second inflatable member when the auxiliary balloon is inflated,
wherein a length of the auxiliary balloon along the longitudinal direction of the flexible band is greater than a length of the second inflatable member along the longitudinal direction of the flexible band, and
wherein the second inflatable member includes one end portion located closer to the first inflatable member in the longitudinal direction of the flexible band and an opposite end portion, the auxiliary balloon including one end portion located closer to the first inflatable member in the longitudinal direction of the flexible band and an opposite end portion, the one end portion of the auxiliary balloon being located at the one end portion of the second inflatable member in a direction orthogonal to the longitudinal direction of the flexible band before inflation of the second inflatable member and the auxiliary balloon.

7. The hemostatic device according to claim 6, wherein the interior of the auxiliary balloon communicates with the interior of the second inflatable member, and further comprising an injection portion connected to the auxiliary balloon to introduce the fluid into the interior of the auxiliary balloon.

8. The hemostatic device according to claim 6, wherein the auxiliary balloon is connected to the second inflatable member.

9. The hemostatic device according to claim 6, further comprising a plate that is more rigid than the flexible band, the plate held by the flexible band, the plate being positioned between a portion of the flexible band and the auxiliary balloon.

10. The hemostatic device according to claim 6, further comprising a plate that is more rigid than the flexible band, the plate possessing an inner surface facing towards the arm when the flexible band is wrapped around the arm in the wrapped state, the inner surface of the plate including a curved portion positioned between the auxiliary balloon and the flexible band.

11. The hemostatic device according to claim 6, further comprising an auxiliary compressing member expandable upon being inflated in response to introducing fluid into an interior of the auxiliary compressing member and disposed between the flexible band and the first inflatable member at a position in which at least a part of the auxiliary compressing member overlaps the first inflatable member to press the first inflatable member when the auxiliary balloon is inflated.

* * * * *